(12) United States Patent
Ray et al.

(10) Patent No.: US 6,962,924 B2
(45) Date of Patent: Nov. 8, 2005

(54) SALT AND POLYMORPHS OF DESLORATADINE HEMIFUMARATE

(75) Inventors: Anup Kumar Ray, Staten Island, NY (US); Hiren Patel, Edison, NJ (US); Mahendra R Patel, East Brunswick, NJ (US)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 10/621,670

(22) Filed: Jul. 17, 2003

(65) Prior Publication Data

US 2004/0058949 A1 Mar. 25, 2004

Related U.S. Application Data

(60) Provisional application No. 60/401,153, filed on Aug. 5, 2002.

(51) Int. Cl.[7] .................. A61K 31/4545; A61K 31/445; C07D 401/04; C07D 401/08; A61P 37/08
(52) U.S. Cl. .......................................... 514/290; 546/93
(58) Field of Search ............................ 546/93; 514/290

(56) References Cited

U.S. PATENT DOCUMENTS

| | | | |
|---|---|---|---|
| 4,659,716 A | | 4/1987 | Villani et al. ............... 514/290 |
| 4,954,503 A | * | 9/1990 | Strupczewski et al. ....... 514/80 |
| 5,290,951 A | * | 3/1994 | Congy et al. .................. 549/59 |
| 5,595,997 A | | 1/1997 | Aberg et al. ................. 514/290 |
| 5,658,899 A | * | 8/1997 | Hansen et al. ......... 514/217.02 |
| 6,100,274 A | | 8/2000 | Kou ............................ 514/290 |
| 6,335,347 B1 | | 1/2002 | Gala ........................... 514/290 |
| 6,506,767 B1 | * | 1/2003 | Schumacher et al. ....... 514/290 |

FOREIGN PATENT DOCUMENTS

| | | |
|---|---|---|
| WO | WO99/01450 | 1/1999 |
| WO | WO 02/42290 A1 | 5/2002 |

* cited by examiner

*Primary Examiner*—Evelyn Mei Huang
(74) *Attorney, Agent, or Firm*—John D. Thallemer

(57) ABSTRACT

This invention provides a process of preparation of novel polymorphic hemifumarate salts of 8-chloro-6,11-dihyfro-11-(4-piperidylidene)-5H-benzo[5,6]-cyclohepta[1,2-b] pyridine, hereinafter called "desloratadine". These polymorphic salt forms show much higher solubility in water and also in protic organic solvents compare to the parent desloratadine. The process of preparing the polymorphic forms comprising:

a) mixing the ethanolic solution of desloratadine and fumaric acid at a temperature of from about 55° C. to 70° C., and stirring for 30 to 45 minutes after mixing, and thereafter filtering the solid thereby prepared in hot condition; to yield the polymorphic form 2 having a DSC of 232° C.±2° C.; or b) mixing the ethanolic solution of desloratadine and fumaric acid at a temperature of form about 15° C. room temperature (25° C.) and stirring at this temperature for 30 to 45 minutes, then filtering at room temperature; to yield the polymorphic form 1 having a DSC of 224° C.±2° C.

21 Claims, No Drawings

SALT AND POLYMORPHS OF DESLORATADINE HEMIFUMARATE

This application claims the benfit of provisional application Ser. No. 60/401,153 Aug. 5, 2002.

FIELD OF THE INVENTION

This invention provides a process of preparation of novel polymorphic hemifumarate salts of 8-chloro-6,11-dihydro-11-(4-piperidylidene)-5H-benzo[5,6]-cyclohepta[1,2-b] pyridine, hereinafter called "desloratadine". These polymorphic salt forms show much higher solubility in water and also in prouc organic solvents compare to the parent desloratadine. In addition, formation of hemifumarate salt imparts to the desloratadine molecule a greater stability than the desloratadine itself. Desloratadine has shown great promise in the treatment as non-sedative antihistamine.

BACKGROUND OF THE INVENTION

It is known that desloratadine as actually used for pharmaceutical formulation has very little or no solubility in water. Another aspect of the drug is that desloratadine is not stable and shows discoloration during stability studies. These dual characteristics of the drug require non-flexible special formulation design to prevent degradation and to retain potency. It has been found (see U.S. Pat. No. 6,100,274) that in solid dosage form desloratadine, containing acidic excipients along with lactose monohydrate resulted in a large amount (14%) of decomposition after one week at 40° C. and 75% relative humidity.

The present invention provides a stable novel desloratadine hemifumarate salt with high water solubility and compatibility with a wide range of excipients for pharmaceutical formulation. The process of preparation of polymorphic form of desloratadine hemifumarate salt produces consistently high quality of the active pharmaceutical ingredient. Stochiometrically one molecule fumaric acid is combined with two molecules of desloratadine.

The invention provides pharmaceutically elegant and desirable properties needed for a drug to be administered to allergic patients, that has excellent color and thermal stability for solid dosage form and is free of undesired solvating agents such as water and organic solvents.

Related patents include:

U.S. Pat. No. 4,659,716 which discloses descarbonylethoxyloratadine possessing antihistaminic properties with substantially no sedative properties. This U.S. patent also discloses methods of making descarbonylethoxyloratadine, pharmaceutical compositions it and methods of using the compositions to treat allergic reactions in mammals. The compound is taught to form salts with fumaric acid among other pharmaceutically acceptable acids.

U.S. Pat. No. 5,595,997 discloses pharmaceutical compositions and methods for treating allergic rhinitis using descarbonylethoxyloratadine.

U.S. Pat. No. 6,100,274 pharmaceutical compositions containing descarbonylethoxyloratadihe.

PCT WO 99/01450 discloses polymorphs of descarbonylethoxyloratadine and pharmaceutical compositions containing them. The polymorph forms are different from those of this invention. Polymorphs of loratadine are disdosed in U.S. Pat. No. 6,335,347.

DETAILED DESCRIPTION OF THE INVENTION

This invention of polymorphic forms I and II of hemifumarate crystalline form of desloratadine refers to the preparation of hemifumarate salt and two novel polymorphs of the compound. This polymorphic salt formation of desloratadine further enhances the scope of formulation development bioavailability.

The present invention discloses a new method of preparation of polymorphic forms I and II of desloratadine hemifumarate that are more stable in different ranges of pH and more soluble in water and or in protic organic solvents. It has been discovered that specific solvent and experimental conditions which consistently produce two distinctly different crystalline polymorphs of desloratadine hemifumarate thereby allowing commercial production of a stochiometrically consistent pharmaceutical product having constant physical properties.

During preparation of desloratadine hemifumarate, two sets of conditions are kept constant.

In one case while mixing the ethanolic solution of desloratadine and fumaric acid, the solution state mixing condition can be from about 55° C. to 70° C. The solution is stirred at this temperature for 30 to 45 minutes after mixing, and the solid filtration is carried out in hot condition. In this situation, the polymorphic form 2 (differential scanning colorimetry, hereinafter "DSC", 232° C.±2°) is generated.

In the other set of conditions, the mixing is at 15° C. to room temperature (25° C.) and is stirred the solution at this temperature for 30 to 45 minutes, then filtered at room temperature. The process and the use of room temperature are preferred to generate the crystalline polymorphic form 1 (DSC of 224° C.±2° C.).

The amounts of the two components of the reaction are employed stochiometrically, with 2 mols of desloratadine to 1 mol of the fumaric acid.

It has been observed that polymorphic form 1 can be changed to polymorphic form 2 under vacuum at 50° C. However, both the polymorphs are stable and do not change: polymorphic form even after crushing in to a solid powder form.

FIGS. 1 and 2 show the difference of polymorphic form 1 and polymorphic form 2 in FT-IR. A clear distinguishable peaks of form 2 at 1085 cm$^{-1}$, 875 cm$^{-1}$, 845 cm$_{-1}$, 755 cm$^{-1}$, 745 cm$^{-1}$, 730 cm$^{-1}$ and 1277 cm$^{-1}$ have been observed whereas these peaks are missing in form 1. A comparison of the hygroscopicity of the polymorphic desloratadine hemifumarate salts (forms 1 and 2) of the present invention and the standard desloratadine free base over a range of relative humidity (RH) of 90% have been studied. The results show a good compatibility of hygroscopicity of the two polymorphic forms of hemifumarate salts with desloratadine standard in DVS. Desloratadine hemifumarate polymorphic form 2 and standard desloratadine show very similar moisture absorption value (0.3%) whereas desloratadine polymorphic form 1 exhibit a little higher value (0.9%).

It has been reported that acidic excipients degrade desloratadine at 40° C. and 75% RH for one week. Desloratadine standard and the two polymorphic forms (polymorphs 1 and 2) were mixed with three volumes of lactose monohydrate and kept at 40° C. and 75% RH for one week, the standard desloratadine showed discoloration whereas two polymorphs retained its crystallinity, color and the texture. This stability study convincingly indicates that polymorphs 1 and 2 are more stable than free base desloratadine under stressed condition. Again, ready conversion of polymorphs 1 to 2 under reduced pressure and temperature identify polymorph 2 as a suitable candidate for solid dosage pharmaceutical composition.

Solubility: Solubility of desloratadine standard and desloratadine hemifumarate polymorphs 1 and 2 were determined photometrically in water, acetate buffer (pH=5.0) and 0.01N HCl at $\lambda_{max}$ 293 nM.

Standard desloratadine: Solubility in $H_2O$=0.010 mg/mL, 0.1N HCl=38.24 mg/mL, acetate buffer (pH=5.0)=12.84 mg/mL.

Desloratadine hemifumarate (polymorph 1): Solubility in $H_2O$=0.441 mg/mL, 0.1N HCl=7.45 mg/mL, acetate buffer (pH=5.0)=1.76 mg/mL.

Desloratadine hemifumarate (polymorph 2): Solubility in $H_2O$=0.553 mg/mL, 0.1N HCl=7.25 mg/mL, acetate buffer (pH=5.0)=1.74 mg/mL.

X-ray powder diffractometry (XRD) study of desloratadine forms 1 and 2 is done in the following manner. The powder of polymorph is filled in an aluminum holder and exposed to CuKα radiation (40 kV×30 mA) in a wide range XRD (Model D5005, Siemens). The instrument is operated in the step-scan mode, in increments of 0.020° 2θ. The angular range is 5 to 50° 2θ and counts are accumulated for 1 second at each step. A typical x-ray diffraction pattern for forms 1 and 2 is as follows, wherein d represents the interplanar spacing and $I/I_0$ represents the typical relative intensities. In the following table (desloratadine hemifumarate forms 1 and 2) only those peaks are listed whose relative intensity $I/I_0$ is equal or greater than 10%.

| POLYMORPH 1 | | POLYMORPH 2 | |
|---|---|---|---|
| d | $I/I_0$ | d | $I/I_0$ |
| 12.32 | 26 | 14.14 | 14 |
| 10.53 | 11 | 10.74 | 13 |
| 8.444 | 19 | 7.158 | 39 |
| 8.149 | 16 | 7.084 | 20 |
| 6.550 | 25 | 5.983 | 12 |
| 6.281 | 22 | 5.663 | 61 |
| 6.185 | 35 | 5.365 | 33 |
| 6.084 | 19 | 5.267 | 100 |
| 5.553 | 88 | 5.064 | 12 |
| 5.373 | 64 | 4.973 | 46 |
| 5.096 | 59 | 4.809 | 16 |
| 4.960 | 41 | 4.745 | 43 |
| 4.745 | 34 | 4.477 | 32 |
| 4.470 | 26 | 4.449 | 26 |
| 4.403 | 30 | 4.399 | 60 |
| 4.365 | 46 | 4.317 | 54 |
| 4.159 | 84 | 4.012 | 49 |
| 4.124 | 73 | 3.772 | 26 |
| 4.061 | 35 | 3.745 | 61 |
| 3.750 | 79 | 3.722 | 97 |
| 3.716 | 100 | 3.590 | 88 |
| 3.659 | 27 | 3.561 | 59 |
| 3.589 | 14 | 3.385 | 24 |
| 3.398 | 11 | 2.986 | 17 |
| 3.362 | 16 | 2.949 | 11 |
| 3.277 | 10 | 2.836 | 20 |
| 3.090 | 23 | 2.778 | 10 |
| 3.051 | 11 | 2.616 | 10 |
| 3.003 | 15 | 2.481 | 12 |
| 2.784 | 10 | | |
| 2.507 | 12 | | |

Pharmaceutical Compositions

Pharmaceutical compositions of this invention may contain in addition to an anti-allergically effective amount of the polymorph form of descarbonylethoxyloratadine as the active ingredient, inert pharmaceutically acceptable carriers that may be solids or liquids. Solid form compositions include powders, tablets, dispersible granules, capsules, cachets and suppositories. A solid carrier can be one or more substances which may also act as diluents, flavoring agents, solubilizers, lubricants, suspending agents, binders or tablet disintegration agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from about 5% to about 20% of the active ingredient. Suitable solid carriers are magnesium carbonate, magnesium stearate, talc, sugar, lactose, pectin, dextrin, starch, gelatin, tragacanth, methycellulose, sodium carboxymethyl-cellulose and a low melting wax, or cocoa butter and the like.

The term "compositions" is Intended to include the formulation of the active compound with encapsulating material as carrier providing a capsule in which the active component (with or without other carriers) is surrounded by carrier, which is thus in association with it. Similarly, caches are included. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for topical administration. Liquid preparations can also be formulated in solution in aqueous polyethylene glycol solution. Aqueous solutions suitable for oral use can be prepared by adding the active component in water and adding suitable colorants, flavors, stabilizing, sweetening, solubilizing and thickening agents as desired. Aqueous suspensions suitable for oral use can e made by dispersing the finely divided active component in water with viscous material, i.e., natural or synthetic gums, resins, methylcellulose, sodium carboxymethyicelluiose and other well-known suspending agents.

Topical formulation useful for nasal or ophthalmic administration is also contemplated. Topical formulation suitable for nasal administration may be solutions or suspensions. Ophthalmic formulations may be solutions, suspension or ointments. Ointments usually contain lipophilic carriers, such as mineral oil and/or petrolatum. Solution for ophthalmic administration may contain sodium chloride, acid and/or base to adjust the pH as well as purified water and preservatives.

The anti-allergic effective amount of the polymorph form of descarbonylethoxyloratadine for topical administration varies from 0.1% to 5% by weight of the total pharmaceutical composition. The preferred amount varies from 0.5% to 2% by weight of the total pharmaceutical composition.

The anti-allergic effective amount of the polymorph form of descarbonylethoxyloratadine for oral administration varies from about 1–50 mg/day, preferably about 2.5–20 mg/day and more preferably about 5–10 mg/day in single or divided doses. The most preferred amount is 5.0 mg, once a day.

Of course the precise dosage and dosage regimen may be varied depending upon the requirements of the patients (e.g., his or her sex, age) as well as the severity of the allergic condition being treated. Determination of the proper dosage and dosage regimen for a particular patient will be within the skill of the attending clinician.

The polymorph form of descarbonylethoxyloratadine possesses antihistaminic properties.

The following examples illustrate the preparation of novel polymorphic forms of desloratadine hemifumarate.

EXAMPLE 1

Preparation of Polymorph 1 of Descarbonylethoxyloratadine Hemifumarate 5.0 g desloratadine is dissolved in 50.0 mL anhydrous ethanol by heating and then allow it to cool to room temperature. The clear solution is cooled by ice water and to it is added 0.875 g anhydrous fumaric acid dissolved in 35.0 mL anhydrous ethanol at room temperature. Addition of ethanolic fumaric acid solution to the cooled ethanolic desloratadine is carried out all at once. After addition the mixture is stirred at cool temperature for 15 minutes and then slowly allowed to come to room temperature and is then stirred at room temperature for 30 minutes. After the stirring the solid is filtered and washed with copious amount of ethanol until the filtrate becomes colorless. The white solid obtained (4.4 g) is first dried in the vacuum pump and then kept in the vacuum oven at room temperature for 2 hours and 30 minutes. DSC shows an endotherm at 224° C.

EXAMPLE 2

Preparation of Polymorph 2 of Descarbonylethoxyloratadine Hemifumarate 5.0 g desloratadine is dissolved in 50.0 mL anhydrous ethanol by heating and then allow it to boil. The clear hot solution is allowed to stir close to the boiling temperature of ethanol and to it is added hot solution of 0.875 g anhydrous fumaric dissolving in 35.0 mL anhydrous ethanol. Addition of hot ethanolic fumaric acid solution to the hot ethanolic desloratadine is carried out all at once. After addition the mixture is stirred at this hot condition for 45 minutes. After the stirring the solid is filtered and washed with copious amount of warm ethanol until the filtrate becomes colorless. The white solid obtained (4.0 g) is the first dried in the vacuum pump and then kept in the vacuum oven at room temperature for 2hours and 30 minutes. DSC shows an endotherm at 232° C.

What is claimed is:

1. Polymorph forms 1 or 2 of descarbonylethoxyloratadine hemifumarate having by the following x-ray powder diffraction pattern expressed in terms of "d" spacing and relative intensities ("RI"):

| POLYMORPH 1 | | POLYMORPH 2 | |
|---|---|---|---|
| d | $I/I_0$ | d | $I/I_0$ |
| 12.32 | 26 | 14.14 | 14 |
| 10.53 | 11 | 10.74 | 13 |
| 8.444 | 19 | 7.158 | 39 |
| 8.149 | 16 | 7.084 | 20 |
| 6.550 | 25 | 5.983 | 12 |
| 6.281 | 22 | 5.663 | 61 |
| 6.185 | 35 | 5.365 | 33 |
| 6.084 | 19 | 5.267 | 100 |
| 5.553 | 88 | 5.064 | 12 |
| 5.373 | 64 | 4.973 | 46 |
| 5.096 | 59 | 4.809 | 16 |
| 4.960 | 41 | 4.745 | 43 |
| 4.745 | 34 | 4.477 | 32 |
| 4.470 | 26 | 4.449 | 26 |
| 4.403 | 30 | 4.399 | 60 |
| 4.365 | 46 | 4.317 | 54 |
| 4.159 | 84 | 4.012 | 49 |
| 4.124 | 73 | 3.772 | 26 |
| 4.061 | 35 | 3.745 | 61 |
| 3.750 | 79 | 3.722 | 97 |
| 3.716 | 100 | 3.590 | 88 |
| 3.659 | 27 | 3.561 | 59 |
| 3.589 | 14 | 3.385 | 24 |
| 3.398 | 11 | 2.986 | 17 |
| 3.362 | 16 | 2.949 | 11 |
| 3.277 | 10 | 2.836 | 20 |
| 3.090 | 23 | 2.778 | 10 |
| 3.051 | 11 | 2.616 | 10 |
| 3.003 | 15 | 2.481 | 12 |
| 2.784 | 10 | | |
| 2.507 | 12. | | |

2. A solid pharmaceutical composition comprising an anti-allergic effective amount of a polymorph form of descarbonylethoxyloratadine hemifumarate of claim 1 and a pharmaceutically acceptable carrier.

3. A solid pharmaceutical composition comprising an anti-allergic effective amount of the polymorph form 1 descarbonylethoxyloratadine hemifumarate of claim 2 and a pharmaceutically acceptable carrier.

4. A solid pharmaceutical composition comprising an anti-allergic effective amount of the polymorph form 2 descarbonylethoxyloratadine hemifumarate of claim 2 and a pharmaceutically acceptable carrier.

5. A method of treating allergic reactions in a mammal which comprises administering to said mammal an anti-allergic effective amount of the either of the polymorph forms of descarbonylethoxyloratadine hemifumarate of claim 1.

6. The process of preparing the polymorph form 1 or 2 of descarbonylethoxyloratadine hemifumarate of claim 1 comprising:

a) mixing the ethanolic solution of desloratadine and fumaric acid at a temperature of from about 55° C. to 70° C., and stirring for 30 to 45 minutes after mixing, and thereafter filtering the solid thereby prepared in hot condition; to yield the polymorphic form 2 having a DSC of 232° C.±2° C.; or b) mixing the ethanolic solution of desloratadine and fumaric acid at a temperature of from about 15° C. to room temperature (25° C.) and stirring at this temperature for 30 to 45 minutes, then filtering at room temperature; to yield the polymorphic form 1 having a DSC of 224° C.±2° C.

7. A 8-chloro-6,11-dihydro-11-(4-piperidylidene)-5H-benzo[5,6]-cyclohepta[1,2-b]pyridine hemifumarate.

8. A polymorph form 1 of 8-chloro-6,11-dihydro-11-(4-piperidylidene)-5H-benzo[5,6]-cyclohepta[1,2-b]pyridine hemifumarate having by the following x-ray powder diffraction pattern expressed in terms of "d" spacing and relative intensity ("$I/I_0$"):

9. A polymorph form 2 of 8-chloro-6,11-dihydro-11-(4-piperidylidene)-5H-benzo[5,6]-cyclohepta[1,2-b]pyridine hemifumarate having by the following x-ray powder diffraction pattern expressed in terms of "d" spacing and relative intensity ("$I/I_0$"):

10. A solid pharmaceutical composition comprising an anti-allergic effective amount of the compound of Claim 1 and a pharmaceutically acceptable carrier.

11. A solid pharmaceutical composition comprising an anti-allergic effective amount of the polymorph form 2 according to Claim 9 and a pharmaceutically acceptable carrier.

12. A solid pharmaceutical composition comprising an anti-allergic effective amount of the polymorph form 2 according to Claim 9 and a pharmaceutically acceptable carrier.

13. A method of treating allergic reactions in a mammal which comprises administering to said mammal an anti-allergic effective amount of the compound of Claim 1.

14. A method of treating allergic reactions in a mammal which comprises administering to said mammal an anti-allergic effective amount of the polymorph form 2 according to Claim 8.

15. A method of treating allergic reactions in a mammal which comprises administering to said mammal an anti-allergic effective amount of the polymorph form 2 according to Claim 9.

16. A process for preparing polymorph form 1 of 8-chloro-6,11-dihydro-11-(4-piperidylidene)-5H-benzo[5,6]-cyclohepta[1,2-b]pyridine hemifumarate comprising:
    (i) mixing desloratadine, fumaric acid, and ethanol at a temperature of from about 15° C. to about 25°0 C. to form a solid; and
    (ii) filtering the solid to form the polymorphic form 1 of 8-chloro-6,11-dihydro-11-(4-piperidylidene)-5H-benzo[5,6]-cyclohepta[1,2-b]pyridine hemifumarate comprising: (i) mixing desloratadine, fumaric acid, and ethanol at a temperature of form about 15° C. to about 25° C. to form a solid; and
    (ii) filtering the solid to form the polymorphic form 1 to 8-chloro-6,11-dihydro-11-(4-piperidylidene)-5H-benzo[5,6]-cyclohepta[1,2-b]piperidine hemifumarate which is characterized by a DSC of 224° C. ±2° C.

17. A process for preparing polymorph form 1 of 8-chloro-6,11-dihydro-11-(4-piperidylidene)-5H-benzo[5,6]-cyclohepta[1,2-b]pyridine hemifumarate comprising: (a) dissolving desloratadine in ethanol to form an ethanolic solution of desloratidine; (b) dissolving fumaric acid in ethanol to form an ethanolic solution of fumaric acid; (c) mixing the ethanolic solution of desloratidine and the ethanolic solution of fumaric acid at a temperature of from about 15° C. to about 25° C. to form a solid; and (d) filtering the solid to form the polymorphic form 1 of 8-chloro-6,11-dihydro-11-(4-piperidylidene)-5H-benzo[5,6]-cyclohepta[1, 2-b]pyridine hemifumarate which is characterized by a DSC of 224° C. ±2° C.

18. The process according to Claim 17 wherein the mixing in Step (c) is conducted for a period of time from about 30 to about 45 minutes.

19. A process for preparing polymorph form 2 of 8-chloro-6,11-dihydro-11-(4-piperidylidene)-5H-benzo[5,6]-cyclohepta]1,2-b]pyridine hemifumarate comprising:
    (i) mixing desloratadine, fumaric acid, and ethanol at a temperature of form about 55° C. to about 70° C. to form a solid; and
    (ii)"filtering the solid to form the polymorphic form 2 of 8-chloro-6,11-dihydro-11-(4-piperidinylidene)-5-H-benzo[5,6]-cyclohepta [1,2-b]pyridine hemifumarate which is characterized by a DSC of 232° C.±2° C.

20. A process for preparing polymorph form 2 or 8-chloro-6,11-dihydro-11-(4-piperidylidene)-5H-benzo[5, 6]-cyclohepta[1,2-b]pyridine hemifumarate comprising:
    (a)' dissolving desloratadine in ethanol to form an ethanolic solution of desloratidine;
    (b)' dissolving fumaric acid in ethanol to form an ethanolic solution of fumaric acid;
    (c)' mixing the ethanolic solution of desloratidine and the ethanolic solution of fumaric acid at a temperature of from about 55° C. to about 70° to form a solid; and
    (d)' filtering the solid to form the polymorphic form 2 of 8 chloro-6,11-dihydro-11-(4-piperidylidene)-5H-benzo [5,6] cyclohepta[1,2-b]pyridine hemifumarate which is characterized by a DSC of 232° C.±2° C.

21. The process according to Claim 20 wherein the mixing in Step (c)' is conducted for a period of time from about 30 to about 45 minutes.

\* \* \* \* \*

UNITED STATES PATENT AND TRADEMARK OFFICE
CERTIFICATE OF CORRECTION

| | | |
|---|---|---|
| PATENT NO. | : 6,962,924 B2 | Page 1 of 4 |
| APPLICATION NO. | : 10/621670 | |
| DATED | : November 8, 2005 | |
| INVENTOR(S) | : Ray et al. | |

It is certified that error appears in the above-identified patent and that said Letters Patent is hereby corrected as shown below:

<u>Column 1</u>, lines 4 and 5 should read:

-- This application claims the benefit of provisional application Ser. No. 60.401,153, filed on Aug. 5, 2002. --.

The allowed claims (8, 9, 11, 12, 16, 17, 19 and 20) have been renumbered as follows:

1. A Polymorph form 1 of 8-chloro-6, 11-dihydro-11-(4-piperidylidene)-5H-benzo[5,6]-cyclohepta[1,2-b]pyridine hemifumarate having the following x-ray powder diffraction pattern expressed in terms of "d" spacing and relative intensity ("$I/I_0$"):

| D | $I/I_0$ |
|---|---|
| 12.32 | 26 |
| 10.53 | 11 |
| 8.444 | 19 |
| 8.149 | 16 |
| 6.550 | 25 |
| 6.281 | 22 |
| 6.185 | 35 |
| 6.084 | 19 |
| 5.553 | 88 |
| 5.373 | 64 |
| 5.096 | 59 |
| 4.960 | 41 |
| 4.745 | 34 |
| 4.470 | 26 |
| 4.403 | 30 |
| 4.365 | 46 |
| 4.159 | 84 |
| 4.124 | 73 |
| 4.061 | 35 |
| 3.750 | 79 |
| 3.716 | 100 |
| 3.659 | 27 |
| 3.589 | 14 |
| 3.398 | 11 |
| 3.362 | 16 |
| 3.277 | 10 |

UNITED STATES PATENT AND TRADEMARK OFFICE
CERTIFICATE OF CORRECTION

PATENT NO. : 6,962,924 B2
APPLICATION NO. : 10/621670
DATED : November 8, 2005
INVENTOR(S) : Ray et al.

It is certified that error appears in the above-identified patent and that said Letters Patent is hereby corrected as shown below:

| | |
|---|---|
| 3.090 | 23 |
| 3.051 | 11 |
| 3.003 | 15 |
| 2.784 | 10 |
| 2.507 | 12 |

2. A Polymorph form 2 of 8-chloro-6, 11-dihydro-11-(4-piperidylidene)-5H-benzo[5,6]-cyclohepta[1,2-b]pyridine hemifumarate having the following x-ray powder diffraction pattern expressed in terms of "d" spacing and relative intensity ("$I/I_0$"):

| D | $I/I_0$ |
|---|---|
| 14.14 | 14 |
| 10.74 | 13 |
| 7.158 | 39 |
| 7.084 | 20 |
| 5.983 | 12 |
| 5.663 | 61 |
| 5.365 | 33 |
| 5.267 | 100 |
| 5.064 | 12 |
| 4.973 | 46 |
| 4.809 | 16 |
| 4.745 | 43 |
| 4.477 | 32 |
| 4.449 | 26 |
| 4.399 | 60 |
| 4.317 | 54 |
| 4.012 | 49 |
| 3.772 | 26 |
| 3.745 | 61 |
| 3.722 | 97 |
| 3.590 | 88 |
| 3.561 | 59 |
| 3.385 | 24 |
| 2.986 | 17 |
| 2.949 | 11 |
| 2.836 | 20 |
| 2.778 | 10 |
| 2.616 | 10 |
| 2.481 | 12 |

UNITED STATES PATENT AND TRADEMARK OFFICE
CERTIFICATE OF CORRECTION

PATENT NO. : 6,962,924 B2
APPLICATION NO. : 10/621670
DATED : November 8, 2005
INVENTOR(S) : Ray et al.

It is certified that error appears in the above-identified patent and that said Letters Patent is hereby corrected as shown below:

3. A solid pharmaceutical composition comprising an anti-allergic effective amount of the polymorph form 1 according to Claim 1 and a pharmaceutically acceptable carrier.

4. A solid pharmaceutical composition comprising an anti-allergic effective amount of the polymorph form 2 according to Claim 2 and a pharmaceutically acceptable carrier.

5. A process for preparing polymorph form 1 of 8-chloro-6, 11-dihydro-11-(4-piperidylidene)-5H-benzo[5,6]-cyclohepta[1,2-b]pyridine hemifumarate according to Claim 1 comprising:

(i) mixing an ethanolic solution of desloratadine and fumaric acid at a temperature of from about 15°C to about 25°C and stirring for 30-45 minutes at this temperature to form a solid; and (ii) filtering the solid at this temperature to form the polymorphic form 1 of 8-chloro-6, 11-dihydro-11-(4-piperidylidene)-5H-benzo[5,6]-cyclohepta[1,2-b]pyridine hemifumarate which is characterized by a DSC of 224°C ± 2°C.

6. A process for preparing polymorph from 1 of 8-chloro-6, 11-dihydro-11-(4-piperidylidene)-5H-benzo[5,6]-cyclohepta[1,2-b]pyridine hemifumarate according to Claim 1 comprising:

(a) dissolving desloratadine in anhydrous ethanol to form an ethanolic solution of desloratadine;
(b) dissolving fumaric acid in anhydrous ethanol to form an ethanolic solution of fumaric acid;
(c) mixing the ethanolic solution of desloratadine and the ethanolic solution of fumaric acid at a temperature of from about 15°C to about 25°C and stirring for 30-45 minutes at this temperature to form a solid; and
(d) filtering the solid at this temperature to form the polymorphic form 1 of 8-chloro-6, 11-dihydro-11-(4-piperidylidene)-5H-benzo[5,6]-cyclohepta[1,2-b]pyridine hemifumarate which is characterized by a DSC of 224°C ± 2°C.

UNITED STATES PATENT AND TRADEMARK OFFICE
CERTIFICATE OF CORRECTION

PATENT NO. : 6,962,924 B2
APPLICATION NO. : 10/621670
DATED : November 8, 2005
INVENTOR(S) : Ray et al.

It is certified that error appears in the above-identified patent and that said Letters Patent is hereby corrected as shown below:

7. A process for preparing polymorph form 2 of 8-chloro-6, 11-dihydro-11-(4-piperidylidene)-5H-benzo[5,6]-cyclohepta[1,2-b]pyridine hemifumarate according to Claim 2 comprising:

(i) mixing an ethanolic solution of desloratadine and fumaric acid at a temperature of from about 55°C to about 70°C and stirring for 30-45 minutes after mixing to form a solid; and
(ii) filtering the solid at this temperature to form the polymorphic form 2 of 8-chloro-6, 11-dihydro-11-(4-piperidylidene)-5H-benzo[5,6]-cyclohepta[1,2-b]pyridine hemifumarate which is characterized by a DSC of 232°C ± 2°C.

8. A process for preparing polymorph form 2 of 8-chloro-6, 11-dihydro-11-(4-piperidylidene)-5H-benzo[5,6]-cyclohepta[1,2-b]pyridine hemifumarate according to Claim 2 comprising:

(a) dissolving desloratadine in anhydrous ethanol to form an ethanolic solution desloratadine;
(b) dissolving fumaric acid in anhydrous ethanol to form an ethanolic solution of fumaric acid;
(c) mixing the ethanolic solution of desloratadine and the ethanolic solution of fumaric acid at a temperature of from about 55°C to about 70°C and stirring for 30-45 minutes after mixing to form a solid; and
(d) filtering the solid at this temperature to form the polymorphic form 2 of 8 chloro-6, 11-dihydro-11-(4-piperidylidene)-5H-benzo[5,6]-cyclohepta[1,2-b]pyridine hemifumarate which is characterized by a DSC of 232°C ± 2°C.

Signed and Sealed this

Twenty-seventh Day of February, 2007

JON W. DUDAS
*Director of the United States Patent and Trademark Office*